US00PP11558P

United States Patent [19]

Murakami

[11] Patent Number: Plant 11,558

[45] Date of Patent: Oct. 10, 2000

[54] PETUNIA PLANT NAMED 'SUNBELKI'

[75] Inventor: Yasuyuki Murakami, Shiga, Japan

[73] Assignee: Suntory Limited, Osaka, Japan

[21] Appl. No.: 09/007,055

[22] Filed: Jan. 14, 1998

[30] Foreign Application Priority Data

Nov. 25, 1997 [JP] Japan ..... 9-10361

[51] Int. Cl.[7] ..... A01H 5/00

[52] U.S. Cl. ..... Plt./356

[58] Field of Search ..... Plt./356

[56] References Cited

U.S. PATENT DOCUMENTS

| | | | |
|---|---|---|---|
| P.P. 6,899 | 7/1989 | Tsuda et al. | Plt./356 |
| P.P. 6,914 | 7/1989 | Tsuda et al. | Plt./356 |
| P.P. 6,915 | 7/1989 | Tsuda et al. | Plt./356 |
| P.P. 8,489 | 12/1993 | Hirabayashi et al. | Plt./356 |
| P.P. 8,768 | 6/1994 | Hirabayashi et al. | Plt./356 |
| P.P. 9,322 | 10/1995 | Tachibana et al. | Plt./356 |
| P.P. 9,341 | 10/1995 | Tachibana et al. | Plt./356 |
| P.P. 9,342 | 10/1995 | Sakazaki et al. | Plt./356 |
| P.P. 9,556 | 5/1996 | Tachibana et al. | Plt./356 |
| P.P. 9,557 | 5/1996 | Suzuki et al. | Plt./356 |
| P.P. 9,754 | 12/1996 | Suzuki et al. | Plt./356 |
| P.P. 10,278 | 3/1998 | Murakami | Plt./356 |
| P.P. 10,279 | 3/1998 | Murakami | Plt./356 |
| P.P. 10,287 | 3/1998 | Murakami | Plt./356 |
| P.P. 10,355 | 4/1998 | Murakami | Plt./356 |

*Primary Examiner*—Howard J. Locker
*Assistant Examiner*—Wendy A Baker
*Attorney, Agent, or Firm*—Burns, Doane, Swecker & Mathis, L.L.P.

[57] ABSTRACT

A new and distinct *Petunia hybrida* variety is provided which forms in abundance attractive small bright yellow blooms with a brown corolla tube. The growth habit is semi-decumbent. The plant is well-branched with substantial secondary branching. High resistance to Powdery Mildew is exhibited. The plant is particularly well suited for ornamental usage as a pot plant or as a bedding plant.

2 Drawing Sheets

BACKGROUND OF THE VARIETY

The Petunia is a very popular plant and is used for flower bedding and potting in the summer season. There are only a few varieties of the Petunia plants which do not have an upright growth habit and which have a high resistance to rain, heat, cold, and diseases. The previously known Petunias of the REVOLUTION Series, such as 'Revolution Purplepink' (U.S. Plant Pat. No. 6,915), 'Revolution Brilliantpink' (U.S. Plant Pat. No. 6,914) and 'Revolution Brilliantpink-mini' (U.S. Plant Pat. No. 6,899) are of the decumBent type, have long stems, a lower plant height, abundant branching, and a high resistance to heat, cold and rain. However, there are only a few varieties having a great profusion of flowers, a yellow flower color, a very small flower size and a high resistance to rain, heat, cold and diseases. Accordingly, this invention was aimed at obtaining a new variety having a yellow flower color, and very small flowers combined with the above features.

The new variety of Petunia plant according to this invention originated as a limb mutant sport which occured as a spontaneous genetic variant of the 'Sunbelchipi' variety (U.S. Plant Pat. No. 10,355).

The new variety of Petunia plant was discovered during April, 1997 in view of its flower color during the propagation of the 'Sunbelchipi' variety at the Omni Nursery Center of SUNTORY Ltd., residing at 863-*1*, Aza-Iketani, Oomori-cho, Youkaiti-shi, Shiga-ken, Japan. The discovered Petunia plant was propagated by the use of cuttings from April, 1997 and then was grown in a bedding and potting trial from Jun, 1997 at the Plant Biotechnology Laboratory of SUNTORY Ltd. The botancial characteristics of the plant were examined, using a similar variety, 'Sunbelchipi', for comparison. As a result, it was concluded that his new Petunia is distinguishable from any other variety, whose existence is known to us, and is stable in its characteristics. The new variety of Petunia plant was named 'Sunbelki' and is botanically classified *Petunia hybrida*. The 'Sunbelchipi' variety was obtained as indicated hereafter.

Initially, 167 seedlings were obtained by crossing a wild type of Petunia plant naded 'C1' as the female parent with another wild type of Petunia plant named 'C2' as the pollen parent in November, 1992. From this crossing, 15 seedlings were selected during spring 1993 in view of their decumbent growth habit and flower coloration. Subsequentyly, 30 seedlings were obtained from a crossing of these selected 15 seedlings in the summer of 1993 and were grown. Sixteen seedlings were selected from these 30 seedlings. These selected 16 seedlings were observed during a trial when potted and when used as bedding plants. The botanical characteristics of finally-selected 16 plants were examined using the similar variety 'Pearl Sky Blue' (unpatented) for comparison from spring, 1994 to spring, 1995. Finally, a single Petunia plant was selected in April, 1995. As a result, it was concluded that this Petunia is distinguishable from any other variety, whose existence is known to us, and is stable in its characteristics. This new variety of Petunia plant was named 'Sunbelchipi'.

The female parent used in the crossing of 'Sunbelchipi' was a wild type of Petunia plant named "C1" (♀) native to Brazil, the seeds of which were gathered at Gramado, Rio Grande Do Sul, Brazil and introduced to Japan in January, 1992. The Petunia plant 'C1' has an erect habit, abundant branching and a great profusion of blooms. The flowers are single, small and have purplish pink colored petals. The leaf shape is elliptic. The Petunia plant 'C1' has a high resistance to rain, heat, drought and pests.

The pollen parent used in the crossing of 'Sunbelchipi' was another wild type of Petunia plant named 'C2' (♂) native to Brazil, the seeds of which were gathered at Gramado, Rio Grande Do Sul, Brazil and introduced to Japan in January, 1992. The Petunia plant 'C2' has a semi-decumbent habit, long stems, abundant branching and a great profusion of blooms. The flowers are single, very small and have reddish purple petals. The leaf shape is lanceolate. The Petunia plant 'C2' has a high resistance to rain, heat, drought and pests. These wild type of Petunia plants 'C1' and 'C2' and 'Sunbelchipi' are presently maintained at the Oumi Nursery Center of SUNTORY Ltd., residing at 863-1, Aza-Iketani, Oomori-cho, Youkaiti-shi, Shiga-ken, Japan.

In the following description, the color-coding is in accordance with the Horticultural Colour Chart of The Royal Horticultural Society, London, England (R.H.S. Color Chart), and the Inter-Society color Council-National Bureau of Standards Color Name (I.S.C.C.-N.B.S. Color Name). Colors from The Japan Color Standard for Horticultural Plant (J.H.S. Color Chart) are also added for reference. The colors set forth are accurate under the growing conditions described for 'Sunbelki'.

The characteristics of the similar variety 'Pearl Sky Blue' used for comparison are as follows.

Plant:
- *Growth habit.*—Medium upright.
- *Plant height.*—14 cm.
- *Spreading area of plant.*—15–17 cm in diameter.
- *Blooming period.*—April to September in the southern Kanto area, Japan.

Stem:
- *Thickness.*—2.7 mm.
- *Pubescence.*—Dense.
- *Branching.*—Abundant.
- *Length of internode.*—1.3 cm.

Leaf:
- *Shape.*—Elliptic.
- *Length. (average).*—5.5 cm.
- *Width. (average).*—3.5 cm.
- *Color.*—Strong yellow green (R.H.S. 144A, JHS 3507).
- *Pubescence.*—Dense.
- *Thickness.*—0.5–0.6 mm.
- *Leaf attaching angle to stem.*—Horizontal to droopy.

Flower:
- *Facing direction.*—Upward.
- *Type.*—Single.
- *Shape.*—Funnel-shape, with five petals.
- *Shape of petal tip.*—Obverse.
- *Waving of petal.*—Weak.
- *Lobation of petal.*—Shallow.
- *Diameter.*—5.5 cm.
- *Color.*—Petal: Strong bluish purple (R.H.S. 88B-76D, JHS 8310). Bottom color of the corolla throat and the outside color of corolla tube: light yellow green (R.H.S. 4C, JHS 3304).
- *Reproductive organs.*—1 normal pistil and 5 normal stamens.
- *Peduncle.*—0.7–0.9 mm in thickness, and 2.7 cm in length.

Physiological and ecological characteristics: Moderate resistance to heat, cold and diseases and peSts. Strong resistance to rain.

The botanical characteristics of the Petunia plant 'Sunbelchipi', which is the parent of the new mutant variety 'Sunbelki', are as follows.

Growth habit: Decumbent to medium.

Plant height: 15–16 cm.

Spreading area of plant: The stem extends to length of 11–13 cm from the base.

Growth: Very vigorous with abundant branching, a great profusion of blooms; the whole bush remaining in bloom for a considerable period of time.

Blooming period: April to late October in the Southern Kanto area, Japan. The plant shape does not change throughout this period.

Stem:
- *Thickness.*—2.3 mm.
- *Pubescence.*—Present.
- *Branching.*—Abundant. The secondary branching is particularly strong.
- *Length of internode.*—1.4 cm.

Leaf:
- *Shape.*—Lanceolate.
- *Length.*—5.1 cm.
- *Width.*—1.6 cm.
- *Color.*—Dark yellow green. (R.H.S. 146B, JHS 3508).
- *Thickness.*—0.2–0.4 mm.
- *Pubescence.*—Sparse.
- *Leaf attaching angle to stem.*—Slanted upward to horizontal.

Flower:
- *Facing direction.*—Horizontal.
- *Type.*—Single.
- *Shape.*—Funnel-shape, with five petals.
- *Shape of petal tip.*—Medium.
- *Waving of petal.*—Weak.
- *Lobation of petal.*—Shallow.
- *Diameter.*—2.8–2.9 cm.
- *Color.*—Petal: Vivid purplish red (R.H.S. 66B, JHS 9707).
- *Bottom color of the corolla throat.*—Strong yellow (R.H.S 11A., JHS 2513).
- *Outside color of corolla tube.*—Light greenish yellow (R.H.S. 4C, JHS 2904).
- *Reproductive organs.*—1 normal pistil and 5 normal stamens.
- *Peduncle.*—0.7–0.8 mm in thickness, and 1.9 cm in length.

Physiological and ecological characteristics: High resistance to rain, heat, drought and peSts, especially resistance to rain and heat is very strong.

This new and distinct variety of Petunia plant, 'Sunbelki', was asexually reproduced by the use of cutting at the aforementioned the Oumi Nursery Center of SUNTORY Ltd., and the homogeneity and stability thereof were confirmed.

SUMMARY OF THE VARIETY

The new varity of Petunia plant 'Sunbelki' has a semi-decumbent habit, long stems and bright yellow flower petals and thus is very different from a similar variety, 'Pearl Sky Blue'. The plant has semi-decumbent habit, a compact plant shape, abundant branching and a great profusion of blooms with the whole plant remaining in bloom for a considerable period of time. The secondary branching is especially strong. The flowers are single, very small and clearly are distinguished from the small flowers of 'Pearl Sky Blue'. The petals have a bright yellow coloration and are unlike the strong bluish purple petals of 'Pearl Sky Blue'. 'Sunbelchipi', The parent of the presnet invention, has a vivid purplish red petal coloration and a strong yellow bottom color of the corolla throat. The new variety, 'Sunbelki' has a bright yellow petal coloration and a strong brown bottom color of the corolla throat and thus is very different from 'Sunbelchipi'.

BRIEF DESCRIPTION OF THE PHOTOGRAPHS

DETAILED DESCRIPTION

Figure 1:
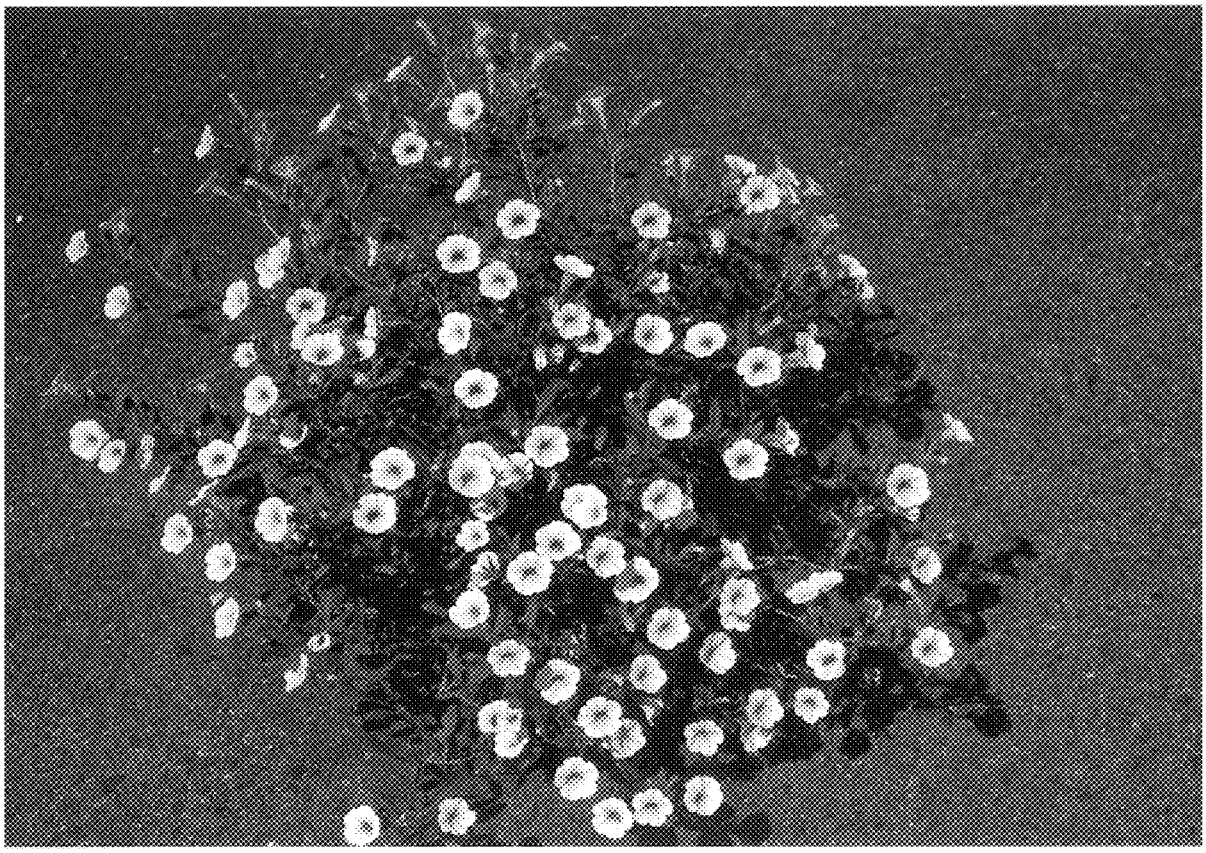
FIG. 1 is a photograph giving a partial view of the new variety of Petunia plant when planted in a flower pot.
Figure 2:
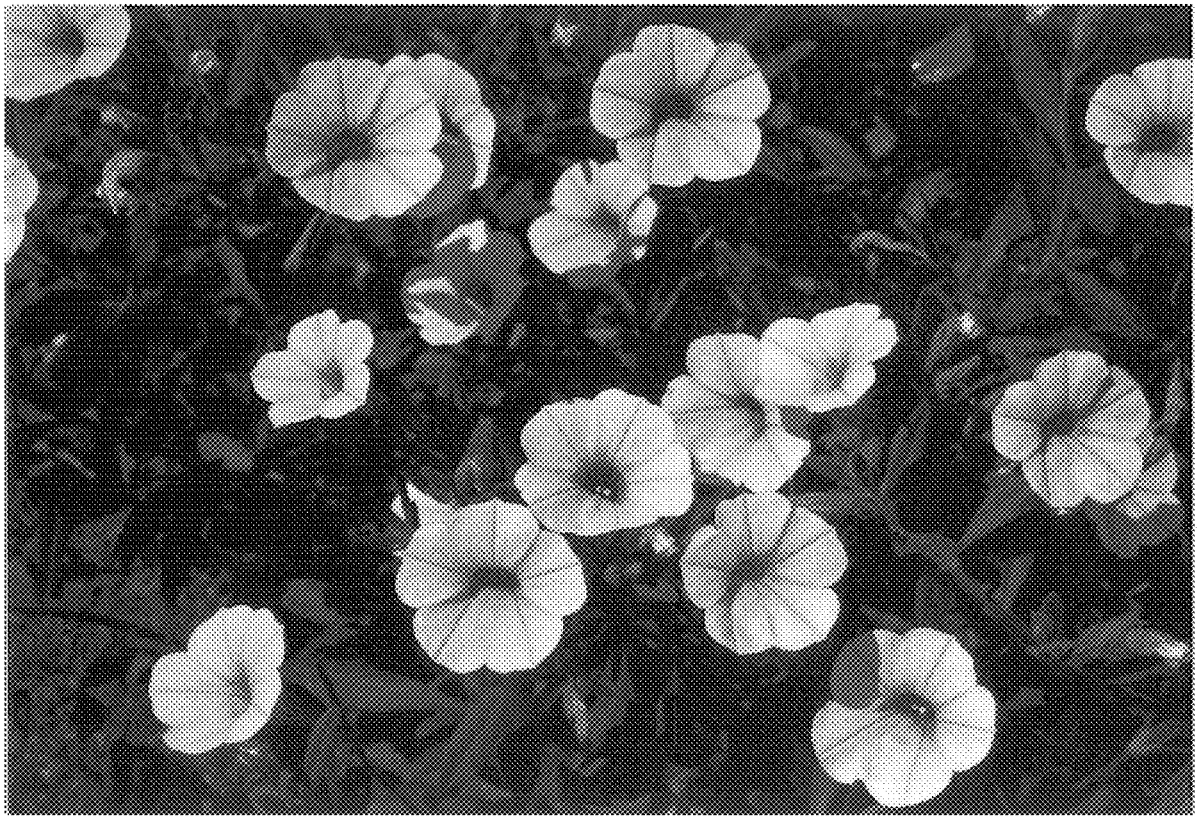
FIG. 2 is a photograph of flowers of the new variety of Petunia plant.

The botanical characteristics of the new and distinct variety of Petunia plant 'Sunbelki' are as follows.

Plant:

*Growth habit.*—Decumbent to medium.

*Plant height.*—18 cm.

*Spreading are a plant.*—The stem extends to length of 18 cm from the base.

*Growth.*—Very vigorous with abundant branching, and a great profusion of blooms with the whole bush remaining in bloom for a considerable period of time.

*Blooming period.*—April to late October in the southern Kanto area, Japan. The plant shape does not change throughout this period.

Stem:

*Thickness.*—23 mm.

*Pubescence.*—Present.

*Branching.*—Abundant with a superior branching propensity. The secondary branches are particularly numerous.

*Length of internode.*—1.5 cm.

Leaf:

*Shape.*—Lanceolate.

*Length.*—5.0 cm.

*Width.*—1.4 cm.

*Color.*—Dark yellow green. (R.H.S. 146B, JHS 3508)

*Thickness.*—0.2–0.4 mm.

*Pubescence.*—Sparse.

*Leaf attaching angle to stem.*—Slanted upward to horizontal.

Flower:

*Facing direction.*—Horizontal.

*Type.*—Single.

*Shape.*—Funnel-shape, with five petals.

*Shape of petal tip.* —Mucronate.

*Waving of petal.* Weak.

*Lobation of petal.*—Shallow.

*Diameter.*—2.8 cm.

*Color.*—Petal: Bright—yellow (R.H.S. 12A, JHS 2505). At low tempertures, it only displays a dark reddish brown (R.H.S. 166A, JHS 1310) main vein and a grayish reddish brown (R.H.S. 165A, JHS 1317) secondary vein on the petals.

*Bottom color of the corolla throat.*—Strong brown (R.H.S. 166B., JHS 1308) with a slightly dark reddish brown (R.H.S. 166A, JHS 1310) veins.

*Outside color of corolla tube.*—Light greenish yellow (R.H.S. 4C, JHS 2904) with a slightly dark reddish brown (R.H.S. 166A, JHS 1310) veins.

*Reproductive Organs.*—1 normal pistil and 5 normal stamens.

*Fertility.*—Seeds are formed, but are infertile under observations to date.

*Peduncle.*—0.7–0.8 mm in thickness, and 1.9 cm in length.

Physiological and ecological characteristics: High resistance to rain, heat, drought and diseases such as Powdery Mildew. The resistance to rain and heat is very strong.

Blooming: A bloom commonly lasts approximately 10 days on the plant. Pinching is not necessary to ensure continued blooming; however, it does tend to enhance bloom production somewhat.

This new variety of Petunia plant 'Sunbelki' is most suitable for flower bedding and potting, particularly in hanging pots or planters, and is further excellent for ground cover usage.

I claim:

1. A new and distinct variety of Petunia plant having the following combinaton of charcteristics:

(a) exhibits a semi-decumbent growth habit with substantial secondary branching;

(b) forms in abundance attractive small single bright yellow blooms having a brown corolla tube, (c) exhibits a high resistance to Powdery Mildew, and (d) is particularly well suited for ornamental usage as a pot plant or for use as a bedding plant;

substantially as herein shown and described.

* * * * *